US008690962B2

(12) United States Patent
Dignam et al.

(10) Patent No.: US 8,690,962 B2
(45) Date of Patent: Apr. 8, 2014

(54) BRAIDED PROSTHETIC SOCKETS WITH ATTACHMENT PLATES AND METHODS OF MANUFACTURE

(75) Inventors: John J. Dignam, Methuen, MA (US); Bradley J. Mate, Epsom, NH (US); Christopher S. Anderson, Epsom, NH (US); Patrick P. McDermott, Vienna, VA (US)

(73) Assignee: Mentis Sciences, Inc., Manchester, NH (US)

( * ) Notice: Subject to any disclaimer, the term of this patent is extended or adjusted under 35 U.S.C. 154(b) by 0 days.

(21) Appl. No.: 13/326,740

(22) Filed: Dec. 15, 2011

(65) Prior Publication Data

US 2012/0179272 A1 Jul. 12, 2012

Related U.S. Application Data

(60) Provisional application No. 61/423,212, filed on Dec. 15, 2010.

(51) Int. Cl.
*A61F 2/80* (2006.01)
*D04C 1/06* (2006.01)

(52) U.S. Cl.
USPC .................................................. 623/33; 87/9

(58) Field of Classification Search
USPC ........... 623/32, 33, 34, 35, 36, 37, 38; 87/8, 9
See application file for complete search history.

(56) References Cited

U.S. PATENT DOCUMENTS

| 5,718,925 | A | * | 2/1998 | Kristinsson et al. | 425/2 |
| 5,824,111 | A | | 10/1998 | Schall | |
| 5,885,509 | A | * | 3/1999 | Kristinsson | 264/314 |
| 5,957,980 | A | * | 9/1999 | Houser et al. | 623/36 |
| 5,971,729 | A | * | 10/1999 | Kristinsson et al. | 425/2 |
| 5,972,036 | A | * | 10/1999 | Kristinsson et al. | 623/33 |
| 6,416,703 | B1 | * | 7/2002 | Kristinsson et al. | 264/257 |
| 7,749,423 | B2 | | 7/2010 | Bader | |
| 2008/0004715 | A1 | | 1/2008 | Asgeirsson | |
| 2008/0234836 | A1 | | 9/2008 | Taylor | |

* cited by examiner

*Primary Examiner* — Marcia Hoffman
(74) *Attorney, Agent, or Firm* — James Creighton Wray

(57) ABSTRACT

This invention provides new above knee (AK) and below the knee (BK) prosthetic sockets and implements specific manufacturing processes for the production of prosthetic sockets through the automated, computer controlled bi-axial and tri-axial braiding of sockets, over a mold or mandrel made of carved foam, plaster material or wax that is a replica of the patient's truncated limb, and is created by a Computer Aided Design (CAD) file controlling a Numerically Controlled (CNC) machine tool. This method of manufacture using aerospace fibers such as graphite or Kevlar, and high performance resins, is used to create a socket which is stronger and lighter weight than conventionally manufactured sockets. Braiding also allows incorporation of woven cloth, tapes and other reinforcements into the braiding process for added strength at selected areas. The method dramatically decreases the production time and cost of the prosthetic relative to conventional methods.

21 Claims, 9 Drawing Sheets

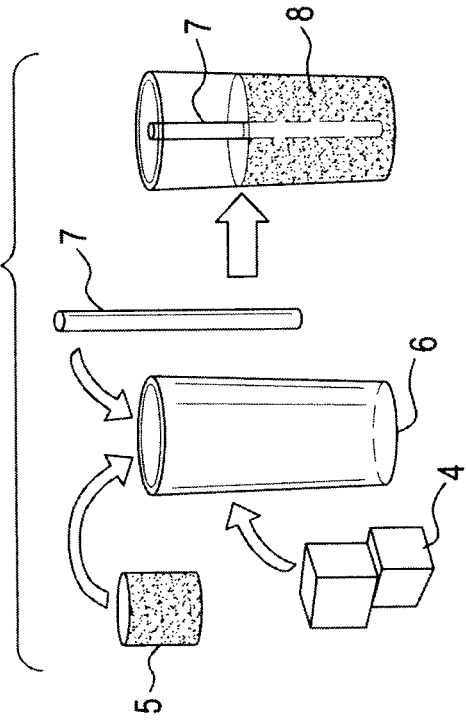
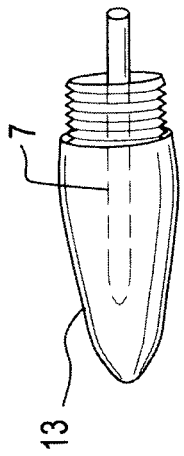
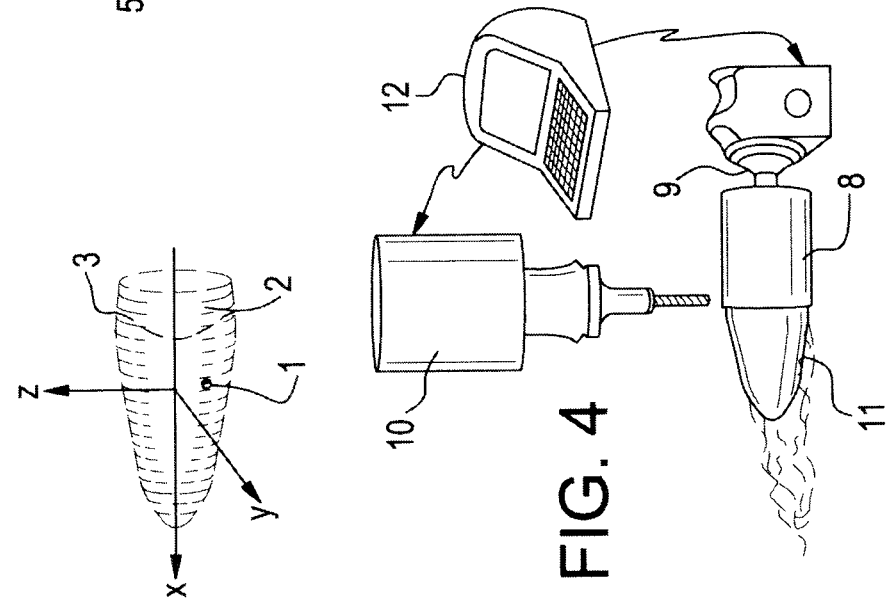

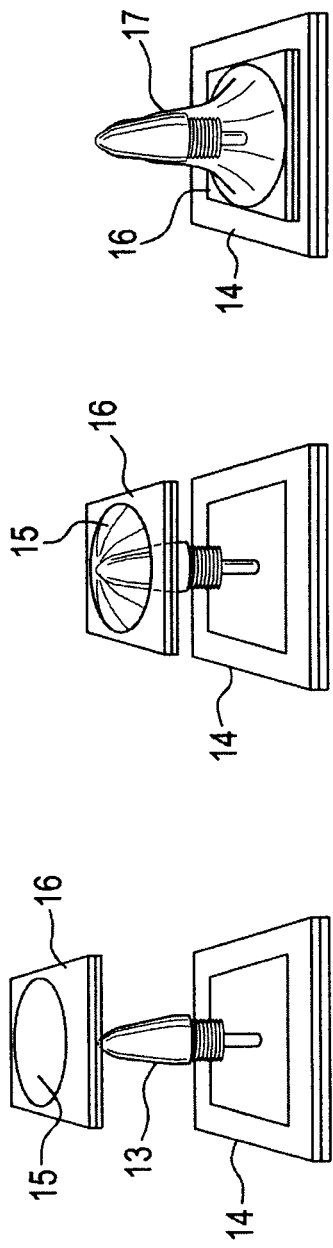

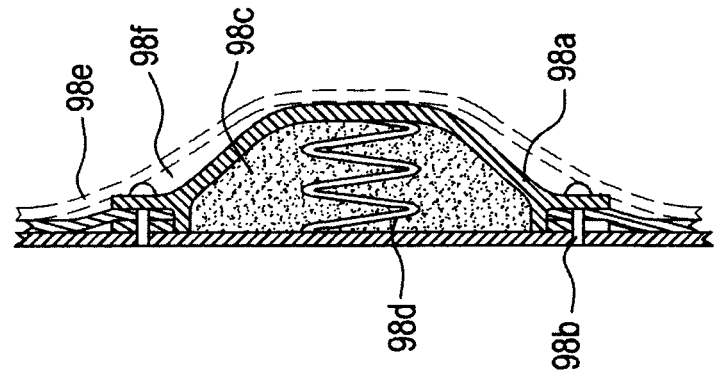
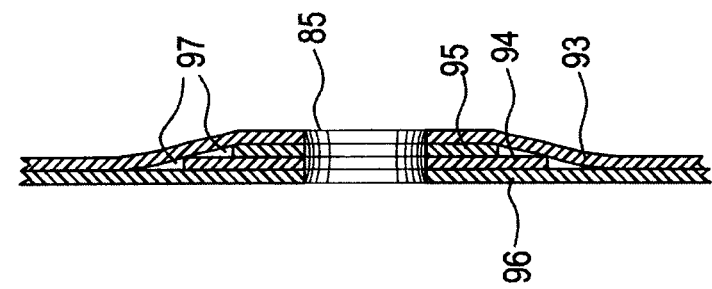
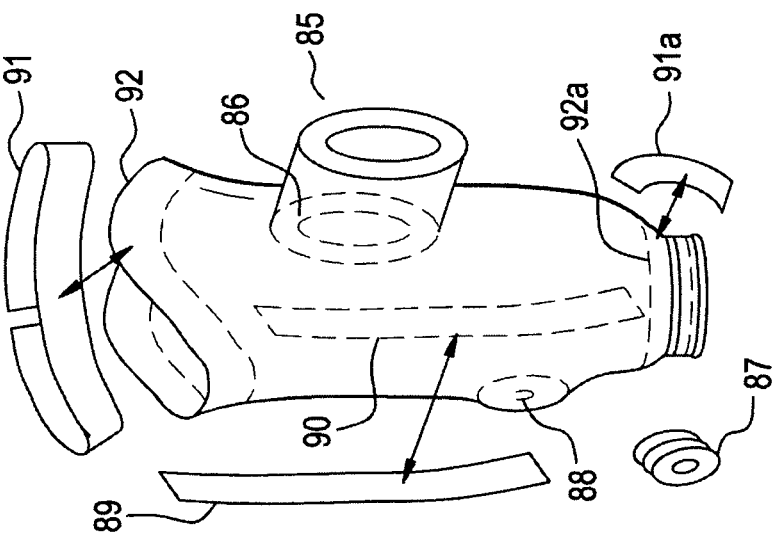

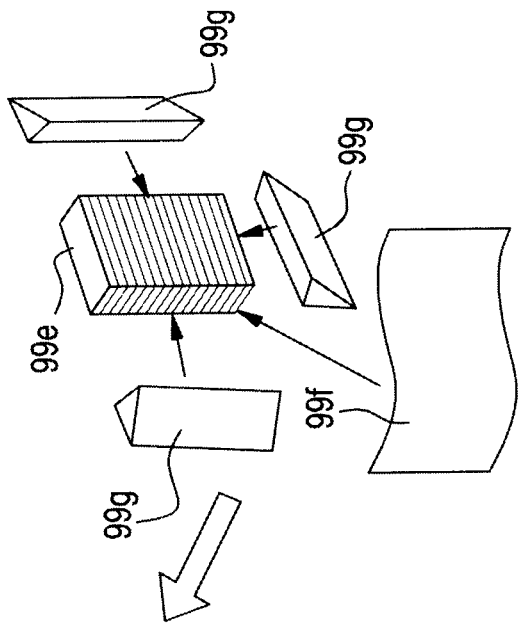
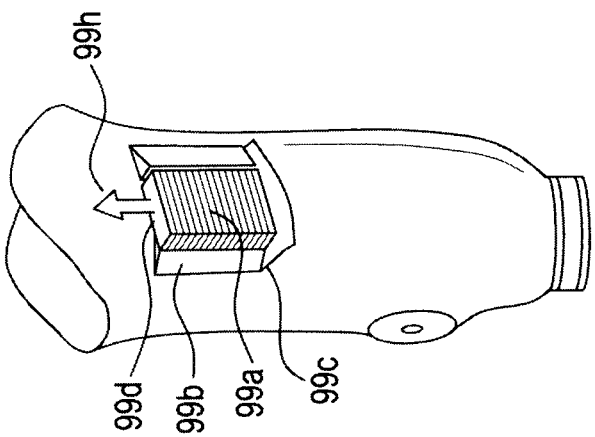

BRAIDED PROSTHETIC SOCKETS WITH ATTACHMENT PLATES AND METHODS OF MANUFACTURE

This application claims the benefit of U.S. Provisional Application No. 61/423,212, filed Dec. 15, 2010, which is hereby incorporated by reference in its entirety as if fully set forth herein.

BACKGROUND OF THE INVENTION

1. Field of the Invention

The present invention relates to processes related to the manufacture of above the knee and below the knee prosthetic sockets using aerospace quality fibers, resins, and textile braiding techniques to produce lighter weight, stronger, lower cost prosthetic products relative to conventional production methods.

2. Description of the Prior Art

Currently, production of trans-tibial and trans-femoral prosthetic sockets starts with the creation of a cast of the patient's residual limb using plaster of Paris wraps or bandages to map the shape of the residual limb. After the wrap has hardened, it is carefully removed and is used as a mold for the casting of a positive plaster mold, a replica of the residual limb, with a pipe embedded in the mold in the axial direction to facilitate handling. After the mold has set, the plaster wrap or bandage is removed.

The plaster mold or cast can be modified by the prosthetics technician, known as a prosthetist, by adding or subtracting material based on the prosthetist's knowledge and experience of the residual limb and its distinctive characteristics in terms of the locations of soft tissue, muscle, and bone. This process of modification is referred to as rectification. The prosthetist uses the cast rectification to produce a better distribution of interface pressures between the socket and the residual limb during usage.

The positive plaster cast is then used as a mandrel or positive form in order to create a negatively formed socket. At this point in the process, a sheet of thermoforming material like polystyrene or PETG is heated until flexible, then drawn over the positive mold, taking care to push the thermoform material into the contours of mold such that the thermoform is a negative replica of the residual limb. The outer surface is then lightly sanded in order to maximize the bonding of subsequent material additions.

Alternatively, instead of casting a positive plaster replica of the limb in the hardened plaster wrap or bandage taken from the patient, some fabrication facilities create a digitized solid model computer file by scanning the inside of the patient's plaster wrap with a mechanical sensor or laser scanner. This digitized image can then be modified by computer software designed for this purpose to dimensionally add or subtract "material" from the digitized image in a manner similar to that of a prosthetist adding or shaving material off the plaster cast to adjust or fine tune the cast to better replicate the truncated limb.

Once the Computer Aided Design (CAD) file is generated, it can then be loaded into computer controlled CNC machine tool often referred to as a "carver", which cuts out a replica of the residual limb in a rigid but malleable material like a high density polymeric foam. At this point, like the process described above for a plaster cast, a thermoforming material is drawn over the positive mold making a negative replica of the limb.

Prior to the formation of the socket, whether from a wax, plaster or high density foam mold, an attachment or adaptor plate is adhered to the bottom or distal end of the thermoset covered mold using an adhesive or harden able putty such as Bondo to secure the plate to the mold, and fill in voids around the plate and the thermoset covered mold. This plate is used to secure the pylon which is essentially a pipe that secures the prosthetic foot to the socket that is fitted to the residual limb, or, in the case of the above the knee socket, attachment to a mechanical knee joint. This attachment plate has a groove around its circumference and in some embodiments, metal straps that can be used to anchor the attachment plate to the materials that form the socket.

The next step in the conventional production process is to secure fabrics (graphite cloth or fiberglass weave) at the distal end of the socket, securing the cloth with wire or other material in the groove of the adaptor plate. The cloth is then added up in several layers around the mold, with a stretchable material drawn over the outside to secure the cloth or weave prior to introduction of a resin matrix material.

The next part of the process involves a Vacuum Assisted Resin Transfer Mold (VARTM) process where a vacuum bag secured around the exterior of the mold with cloth layup contains the resin which is poured into the top of the composite assembly and manually "massaged" down the socket assembly to assure the cloth laminate is fully wetted. After the resin is cured, the plaster has to be chipped out of the socket and interior and exterior surfaces cleaned prior to use. This conventional process suffers from a number of drawbacks. One, the wrap-casting process is somewhat messy and labor intensive as are many of the subsequent steps in the formation of the socket. Secondly, if the prosthetist does not make a digitized solid model of the limb, there is not a permanent record of either the initial plaster wrap representing the shape of the residual limb, or the subsequent negative plaster mold, or, more importantly, the rectified plaster mold, since it has to be broken out the mold to complete the production of the socket. Since there is no record of the shape of the residual limb, the whole process has to be repeated if a socket is damaged or lost, or needs minor adjustments later.

The need exists for improved methods and structures for making prosthetic sockets.

SUMMARY OF THE INVENTION

This invention provides new above knee (AK) and below the knee (BK) prosthetic sockets and implements specific manufacturing processes for the production of prosthetic sockets through the automated, computer controlled bi-axial and tri-axial braiding of sockets, over a mold or mandrel made of carved foam, plaster or thermoset material in the conventional manner, but also of an easily retrievable and usable wax or water soluble casting material created by a Computer Aided Design (CAD) file on a Numerically Controlled (CNC) machine tool. The CAD file is created from a 3-D digital image of the patient's residual limb generated by a laser scanner or other sensing mechanism. This method of manufacture using aerospace fibers such as graphite or Kevlar, and high performance resins, is used to create a socket which is stronger and lighter weight than conventionally manufactured sockets, and generates a very accurate negative replica of the patient's residual limb, thus adding to the comfort of the patient. Braiding also allows incorporation of woven cloth and reinforcements into the braiding process for added strength at selected areas, for example, where cut outs may be desired or appliances added to the base socket structure. The method also dramatically decreases the production time and cost of the prosthetic relative to conventional methods, which are very labor intensive. The CAD file can be retained for future use in the generation of additional sockets which may be needed to replace lost or broken sockets The manufacturing process described in this invention, the production of sockets through automated, computer controlled bi-axial or tri-axial braiding of the new sockets, circumvents many of the drawbacks in conventional production cycles cited above. As will be seen in the description of the invention, the braiding process is initiated over a mold or mandrel which could be made conventionally with a plaster or thermoset mold or as described in the current invention by an easily retrievable and re-usable wax or water soluble casting material. The wax mold, created by a CAD file on a CNC machine can dramatically decrease the production time and cost.

The sockets produced in this manner by the textile braiding process are stronger and lighter weight. The lighter weight especially benefits the patient, since weight of the prosthetic is often linked to other secondary effects like hip problems induced by heavy prosthetic limbs. The automation of the braiding process as described in this invention allows the operator to "engineer" the socket during the production process, by varying the lay down of fiber or fiber tow on the mandrel by adjusting the speed of the gantry and braider to open up and/or close the braid, thus adjusting the angle between the fibers or tows. This affects the fiber density which is also adjustable, depending on the strength requirements of the socket. By regulating the tension on the fibers, the operator is also able to achieve a more compact weave of fibers. This has an additional beneficial effect, from a cost and weight point of view, of requiring less resin.

Since more strength is required, for example, on the distal end of the socket, at the attachment point, the operator is able to apply more fiber at that point and back off the density at the mid-section or proximal end of the socket, thus saving on the amount of fiber required for the socket. The "engineered" socket with reinforcements at the distal end can be fabricated in most cases with only two layers of braided fiber, verses four layers of graphite weave which is more common in the prosthetics fabrication industry.

Accordingly, it is a principal object of the invention to apply automated composite manufacturing processes (braiding) to the production of an improved prosthetic sockets using 3-D digital images of the residual limb to produce mandrels that are replicas of the residual limb of the patient.

It is another object of the invention to use the flexibility of the braiding process to reduce the amount of fiber or fiber tow, as well as resin, to produce an "engineered" socket that is lighter weight than conventionally produced sockets.

It is another object of the invention to integrate a braider manufacturing cell where the operator can adjust the gantry and braider speeds, as well as tension on the fiber or fiber tow so that the composite requires less fiber and resin while maintaining the necessary socket strength for the patient.

It is another object of the invention that mandrels made of wax, along with the shavings resulting from the carving process, can be melted down and reused in subsequent operations.

It is another object of the invention to reduce manufacturing costs through reduced direct labor and materials costs, including recycling and reuse of materials.

It is another object of the invention to improve durability and strength of the socket and attachment hardware, which allows for the production of lighter weight sockets.

It is another object of the invention to closely match the contours of the truncated or residual limb which adds to the comfort of the patient.

It is another object of the invention to retain a 3-D digital image of the prosthetic socket to facilitate modification of the socket for improved fit, and/or remanufacture a socket if lost or damaged.

It is another object of the invention to accomplish the whole manufacturing process in a much shorter time than conventional processes, thus further reducing cost and inconvenience to the patient.

It is also an object of the invention to incorporate woven cloth made from high performance fibers, between the layers of braided material to strengthen and reinforce areas of the socket where cutouts are required to relieve pressure on the truncated limb.

It is also an object of the invention to facilitate adding appliances to the base structure which are easily secured by the braiding process.

The overall prosthetics manufacturing process can be summarized as follows: 1) The patient's needs are identified including height, weight, and specific purpose of the socket; 2) A 3-D model of the residual limb is created using various sensing techniques, such as laser scanners; 3) Molds are created using computer controlled machine tools; 4) The 3-D model can modified to allow for foam liners, limb attachment points or other special requirements; 5) The mold is used as a mandrel in a bi-axial or tri-axial braiding machine which forms varied layers of fibers, impregnated with resin; 6) The resin is cured; 7) An attachment plate is added and reinforce with additional braiding.

These and further and other objects and features of the invention are apparent in the disclosure, which includes the above and ongoing written specification, with the claims and the drawings.

BRIEF DESCRIPTION OF THE DRAWINGS

Various features and attendant advantages of the present invention will become more fully appreciated when considered in conjunction with accompanying drawings, wherein:

FIG. 2 is a perspective view of a generalized digital file of a 3-D virtual image of a residual limb.

FIG. 3 is a perspective view of the production of a mold blank from wax or water-soluble mold material with pipe or rod inserted for handling.

FIG. 4 is a side view illustrating the milling of the blank mold with computer controlled CNC machine tool to produce a positive replica of the residual limb.

FIG. 5 shows the completed mold with the attachment rod, removed from CNC tool.

FIGS. 6a, 6b, and 6c show the sequence of steps where a frame containing a sheet of heated thermoplastic material (6a) is pulled down over the mold (6b) to form a thin thermoplastic outer layer on the mold (6c).

FIG. 7 is a side schematic view of the gantry feeding the mandrel mold into the braider, with computer and manual controls.

FIG. 8 shows application of resin to the braided layers on the mandrel as it emerges from the braider.

FIGS. 18*a*, 18*b*, and 18*c* illustrate additional reinforcements, weave or cloth inserts or tapes, (18*a*), to provide added strength for cutouts (18*b*), or additional appliances (18*c*), or weave tapes added to the distal end to secure the attachment plate.

FIGS. 19*a* and 19*b* shows the incorporation of a pouch structure on the surface of the socket that can house removable electronics packages, including batteries, to power microprocessor driven prosthetic articulating knee and ankle joints.

DETAILED DESCRIPTION OF THE PREFERRED EMBODIMENTS

Figure 1:
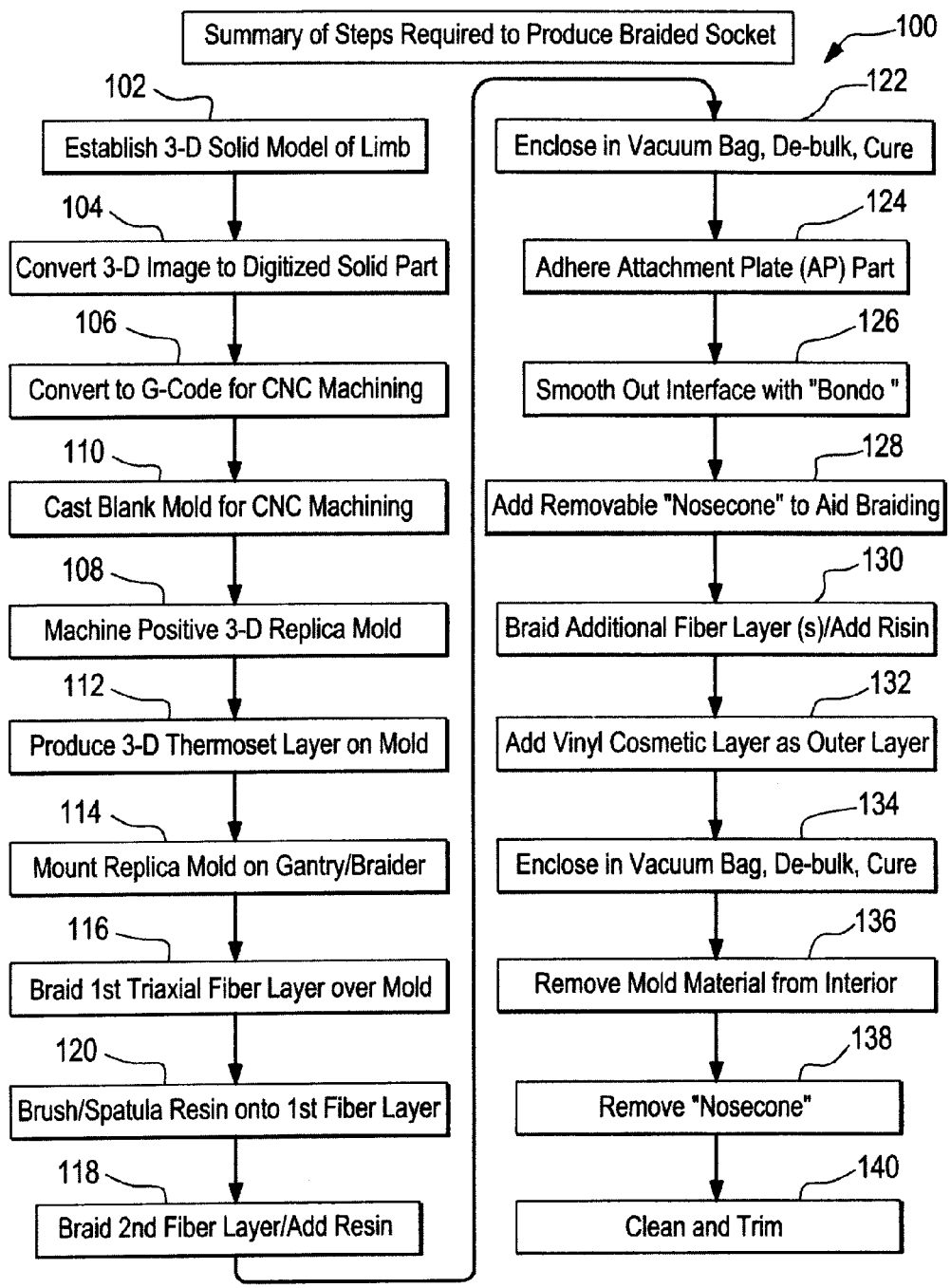
FIG. 1 is a flow chart illustrating a step-by-step process for producing the new braided socket.

FIG. 1 illustrates the step-by-step process for the fabrication of the braided socket 100 with an attachment plate, beginning with the 3-D solid model 102 of the residual limb, which is converted to a digital solid part file 104, and then to G-code 106, which controls the milling machine fabrication 108 of a positive replica of the residual limb from the cast blank mold 110. A thin thermoplastic layer is produced on the mold 112 which can strengthen the mold during the braiding process and create a smooth inner surface in the final product. The replica mold is then attached to the gantry 114, which inserts the mold mandrel into the braider, where layers of fiber are laid down 116. The resin is applied manually 120 between layers 116, 118 by brush, spatula or spray, and the assembly is then vacuum bagged, de-bulked and cured 122. An attachment plate is affixed 124 to the distal end of the cured assembly. The interface between the socket and the attachment plate is smoothed 126 with adhesive or hardenable putty. An optional removable nose cone is attached 128 to the attachment plate to aid braiding, and additional layers of fiber are laid down and resin added 130 to secure the attachment plate after the sacrificial nose cone is applied to aid in the braiding. A vinyl "cosmetic" layer 132 is added while the resin is wet, and adhered to the assembly through the vacuum bag process described above. The product is enclosed in a vacuum bag, de-bulked, and cured 134. The wax or other soluble material is removed from the interior of the assembly 136. The nose cone is removed 138. The socket is then cleaned and trimmed to fit the residual limb 140.

The above description is one way of producing a prosthetic socket. There are many variations to the production cycle which utilize braiding, but may differ in one or more details depending on the practice and skill of the technician. In step 112, for example, instead of producing a thermoplastic layer on the mold, a PVA bag can be pulled over the mold and subsequently braided over with the first layer of braid. Instead of brushing on resin manually in step 120, resin can be applied in the conventional manner by Vacuum Assisted Resin Transfer Molding VARTM techniques.

FIG. 2 shows a 3-D model or virtual image 1 of the residual limb which can be produced by a number of means: a) the residual limb is scanned with a laser imaging system, a touch sensor, visible image or other external surface sensor; b) data from an MRI or X-Ray of the residual limb is converted to a 3-D model; c) a plaster cast matching the residual limb produced by conventional means described above, can also be scanned to produce a 3-D virtual image. In creating the 3-D model, an extension 2 is built in to aid in the braiding of the socket beyond that which is required for matching the residual limb. Extension 2 will be trimmed off at the end of the process along a trim line 3 to provide and accurate and clean edge at the proximal end of the socket.

The 3-D model, with x, y, and z axes, is then converted through software to a digitized solid part file, which in turn is converted to a standard G file, for control of the computer controlled CNC machine tool. This tool will form the positive image of the residual limb on a cylindrical blank mold.

FIG. 3 shows the formation of the cylindrically-shaped blank mold is produced by pouring heated wax 4 or by adding a water soluble particle-based mold material 5, such as Aquapore, into a cylindrically shaped metal container 6. The blank mold material must be strong enough to act as a mandrel for the braiding machine, but can be remove easily from the interior of the socket part at the last stages of production through the melting of the wax or flushing out of the Aquapore material. The blank mold need not necessarily be cylindrical in shape, but can be cast into other shapes like truncated cones which more closely match the final socket shape. During the formation of the blank mold, a pipe or rod 7 is secured in the center of the mold 8 along the axis of the cylinder 6. This will act as a means for handling the blank mold and attaching it to the various machines required in the manufacturing processes. Care is taken so that any mismatched thermal expansion will not cause the mold to crack or distort if a high temperature cure processes is later required.

FIG. 4 shows the blank mold 8 attached to the spindle 9 of the CNC machine 10 in order to mill a 3-D replica 11 of the residual limb. The machining operation is performed so that the socket mold is concentric with the rod, which will then inherently be concentric with the braiding machine. The Computer Aided Manufacturing (CAM) process uses a multi-axis machining tool to fabricate the male mold automatically. The CAD model driving this process can also serve as the framework for developing an engineered solution for customized sockets where finite element analysis FEA software is used to optimize the laminate (fiber, matrix, architecture) according to the patient's weight, and anticipated activity scope. The specific machine requirements include minimum of 4 axes of control including 3 translational and 1 rotational. The machine is capable of machining several sizes to accommodate various designs. The machine tool is controlled by a computer 12 with the digitalized solid part file converted to G-Code as previously discussed. Software is used to convert a 3D solid model into a machine control program. A user friendly graphical interface has been developed so that the solid model can be easily be imported by the operator to control the CNC machine.

FIG. 5 shows the finished part 13 from the milling process, with attachment pipe 7 embedded in the mold.

FIG. 6a shows finished part 13 mounted on a stand 14 for production of a thin thermoplastic overlay 15 on the mold 13. Using the milled piece 13 as a mandrel, a thin layer of transparent thermoset material like Polystyrene, or PETG 15, mounted in a frame 16, is heated until flexible.

FIG. 6b shows the flexible thermoplastic sheet 15 being pulled down over the mold 13, producing a negative image of the limb as shown in FIG. 6c. This plastic negative replica 17 can remain on the mold to strengthen it, or can be removed from the mold and used by the prosthetist as a "check socket" where the thin transparent mold 17 can be refitted on the patient to detect pressure points or other anomalies that could be used to modify the original mold to assure a better fit. The thermoplastic replica 17, as we shall see later in the discussion, can also form the smooth interior surface of the braided socket if it remains on the mold as the fibers are braided to form the composite socket.

Figure 10C:
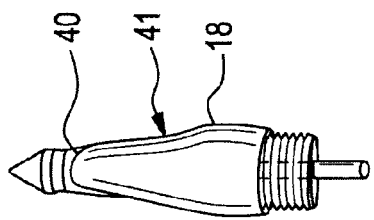
FIGS. 10a, 10b, and 10c show exploded views of an attachment plate (10a), affixed to the tip of the braided assembly, with a removable nosecone affixed to the attachment plate (10*b*) with the interface smoothed out with harden-able putty (10*c*).
Figure 10B:
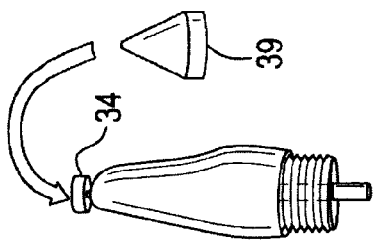
Figure 10A:
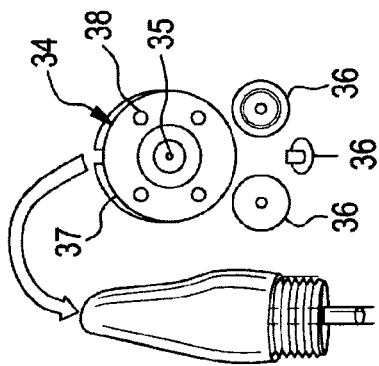

At this point of the process, an attachment plate shown as 34 in FIG. 10a can be affixed directly to the distal end of the thermoplastic replica with procedures shown in FIG. 10, prior to the commencement of any braiding process. In this case, the mandrel and the attachment plate are braided together with layers of fiber overwrapping the attachment plate during the first and subsequent laying down of the layers of braid. Or, the braiding can commence without the attachment plate as shown in FIG. 8, with the attachment plate added later for subsequent layers of braiding that over wrap the attachment plate.

FIG. 7 shows the manufacturing system that includes a carrier system (braider) 20 and a linear carrier (gantry) system 19 that are controlled in this case with two Contrex, M-Trim controllers. The M-Trims are controlled with RS-422 communication ports that are interfaced with a standard desktop computer 23. The mold assembly 18 is mounted on the gantry 19 positioned in the center of the braiding machine 20. During manufacture, the gantry feeds the mold assembly back and forth through the braider as the various layers of fiber 21 are laid on the mandrel 18.

The braider 20 is surrounded by an environmental enclosure 22 made with transparent plastic so the operator can view the part as it is being made. The environmental enclosure is maintained at a negative pressure, by a filtering system, to removes graphite or other particles generated during braiding.

The speed of the gantry 19 feeding the mandrel 18 and the speed of braider 20 laying down fiber 21 is controlled by the computer 23 with software which automatically adjusts the speeds of each in order to achieve the optimal angle and density of fibers laid down. The operator is also able to control the process via a manual controller 24.

Mentis Sciences Computer Automated Braiding System (MSCABS) developed by Mentis Sciences Incorporated, MSI, is used to fabricate accurate, and repeatable, state of the art textile structures. This is accomplished by collecting feedback data such as braid speed and gantry position, and using this to calculate and continuously control the braider and gantry speeds and create the desired laminate composite structure.

The control speeds are determined by the geometry of the part being fabricated (specified by CAD model) and with user input providing braid angles that are determined by patient requirements. By controlling braid angle as a function of axial location and ply number, the system can tailor the mechanical properties of the structure being fabricated to the needs of the patient's prosthetic requirements. This technology thus enables efficient manufacturing of complex, patient-specific prosthetic sockets.

The computer automated textile braiding (CATB) techniques have been developed specifically for 2D bi-axial and tri-axial braided textile preforms. These techniques and fabrication processes significantly reduce the fabrication time and cost associated with conventional techniques, and they are well-suited to the fabrication of prosthetic sockets. The CATB is the interface between the CAD model and desired laminate architecture. It enables a user to braid onto an axisymmetric cross section control or vary the fiber braid angle and subsequently the coverage factor and the fiber volume fraction In summary, a computer controlled braiding system consisting of a rotating multi-carrier mechanism mounted to a precision linear drive system has been developed to allow for the fabrication of complex, net-shape braided structures to be created in a completely automatic manner.

FIG. 8 shows the lay down of the first layer of graphite or other fiber 21 over mold 18 using a tri-axial braiding scheme with axial fibers 25 interleaved with radial fibers 26 laid down on the circumference of the mold. The second or subsequent layers of fiber can be laid down in like manner with axial fibers 25 offset from previous layer to distribute loadings.

In alternative schemes, a bi-axial braiding process can be used, with tows of fibers laid down on the mandrel at varying angles relative to each other to add axial strength to the product thus eliminating the need for an axial braid in the tri-axial braiding scheme.

Figure 17A:
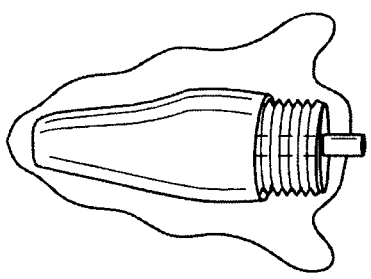
FIGS. 17*a*, 17*b*, and 17*c* illustrate an alternate more conventional means of adding resin to the braided product (17*a*) with resin poured into the top of a PVA bag (17*b*) with bag removed after curing (17*c*).
Figure 17B:
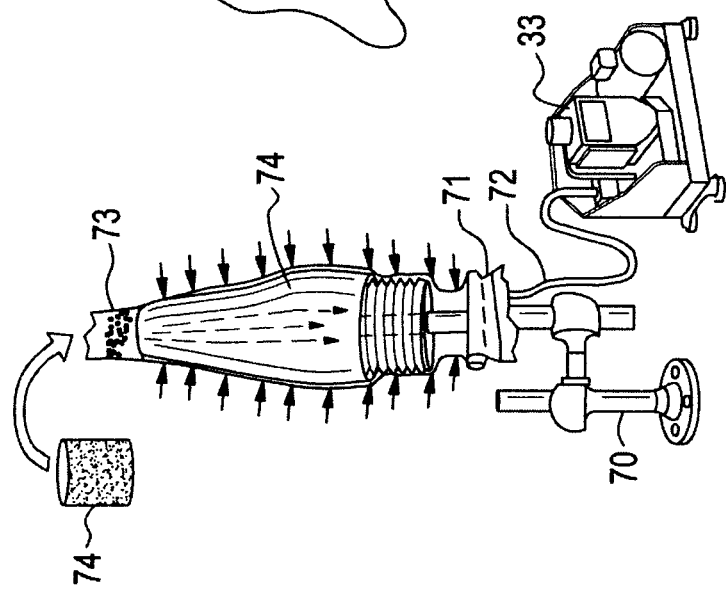
Figure 17C:
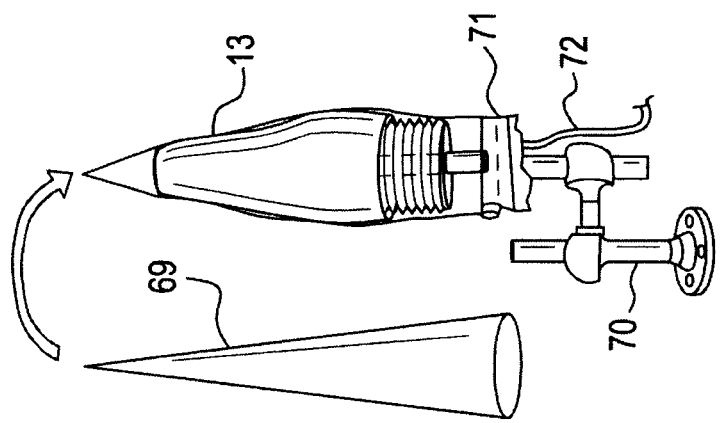

The figure shows resin being applied manually with a brush 26, which is only one of several means of applying the resin. Once the first layer is laid down on the mandrel, resin can be sprayed, rolled or brushed on manually, or applied manually with a spatula and smoothed out over the first layer of fiber. The important point here is that amount of resin applied can be carefully controlled by the operator to avoid waste and assure even distribution of resin. An alternate method, to be described later, is shown in FIGS. 17a, 17b, and 17c.

Figure 9C:
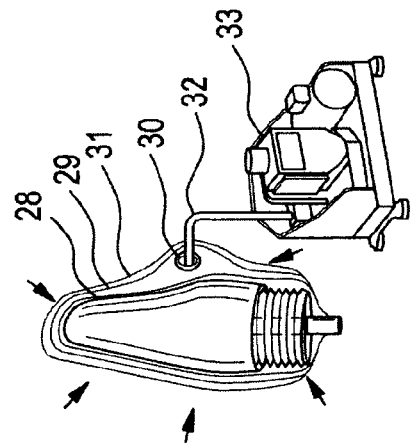
FIGS. 9a, 9b, and 9c show a sequence where layers of material (6a) including an outer vacuum bag are loosely wrapped around the mold (6b) and evacuated (6c) to consolidate the assembly.
Figure 9B:
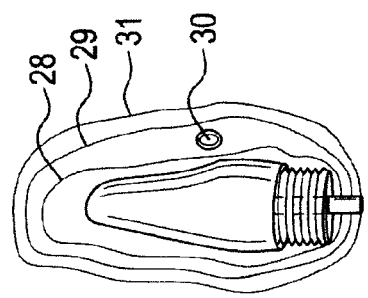
Figure 9A:
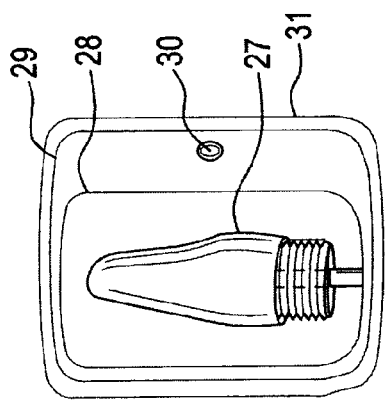

FIG. 9a shows the consolidation process when the resin is manually applied as shown in FIG. 8. In this process, layers of material are required for vacuum bagging and consolidation of mold 27 with first layer being a peel ply 28, then with a breather cloth 29, with a vacuum fitting 30 on the breather cloth and an outer layer 31 serving as the vacuum bag. FIG. 9b shows the loose wrapping and taping of the various layers over the mold. FIG. 9c illustrates the consolidation of the fiber layers with attachment 32 of a vacuum pump 33 to the vacuum fitting 30 and evacuation of the assembly until the fiber layers are compressed or debulked. The assembly is then is cured at an appropriate temperature. Curing factors may include temperature, pressure, vacuum and time. The required temperature and pressure is dependent by the resin type (thermo-plastic, or thermo-set). After curing the wrappings 28, 29, and 31 are removed.

FIGS. 10a, b, and c show various attachments to the assembly prior to final consolidation. FIG. 10a shows an exploded view of a fixture called an attachment plate 34, with an expulsion valve 35 in the center with internal valve hardware 36 displayed. The valve 35 is used to secure the socket on the residual limb with a partial vacuum when the socket is fitted to the limb. The flat cylindrically-shaped attachment plate has a grove 37 in the outer circumference which in subsequent steps will be braided over to more firmly secure the attachment plate to the socket. The attachment plate 34 has threaded sites 38 for bolting the prostheses pylon to the socket. The pylon is essentially a pipe for attaching the prosthetic foot to the socket. FIG. 10a shows attachment plate 34 with internal valve hardware 35 being attached to the distal end of the socket with an adhesive.

FIG. 10b shows a conical foam nosecone 39 being attached to the base of the attachment plate 34 to aid in the braiding process. This removable nosecone temporarily attached to the base of the attachment plate is there to provide a better termination of the braid, which would be difficult over the flat surface of the attachment plate. The nosecone 39 is needed only if the braiding commences from the smaller distal end of the mandrel and proceeds to the larger proximal end. If the braiding commences at the proximal end of the mandrel, the gantry can be reversed at the distal end of the attachment plate 34 without having to go beyond the plate, with a second layer of braiding laid down on the mandrel, with the braiding process terminated at the proximal end.

FIG. 10c shows a material addition 40 to the interface of the attachment plate to the socket. Since the radius of the outer circumference of the cylindrically-shaped attachment plate 34 is dimensionally larger than the distal or tip end of the of the socket mold 18 to which it is attached, there is a need to smooth out the interface by applying a harden-able putty, such as Bondo, for example, to the interface, to provide a smooth transition from the socket to the attachment plate. This new assembly 41 becomes the new mandrel for additional processing.

Figure 11:
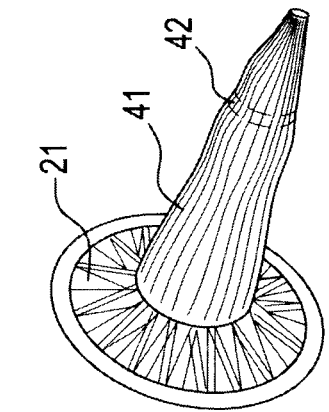
FIG. 11 is a perspective view of the object in FIG. 10*c* braided end-to-end.

FIG. 11 illustrates later stages in the manufacturing process where one or more layers of braided fiber 21 are braided over the extended mold 41, with the braider and gantry speed reduced by means of the manual controller 24 (FIG. 7) at the location 42 which corresponds to the groove 37 (FIG. 10a) in the attachment plate circumference as described previously. This is done so that additional fibers 5 are laid down to increase the strength of the socket/attachment plate interface. This location is often the place where conventionally manufactured sockets fail due to high torsional stress. Resin is again applied to each layer as it is laid down, as shown in FIG. 8.

Figure 12:
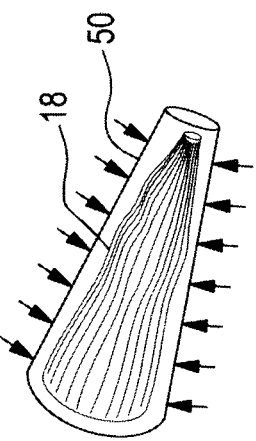
FIG. 12 illustrates the application of an outer cosmetic layer for finishing the socket with vacuum bagging and evacuation to consolidate the part.

In FIG. 12, an additional step is undertaken to provide a smooth and attractive finish to the socket. An outer layer 50 of vinyl or other material is applied to the mold 18 while it is wet with resin. This "cosmetic" layer 50 may be flesh colored or have designs chosen by the patient to provide an attractive aspect to the prosthetic socket. The mold 18 with outer cosmetic layer 50 is then wrapped with the peel wrap 28, breather layer 29 and outer vacuum bag 31 and consolidated or debulked with the vacuum pump as shown in FIG. 9.

Figure 13:
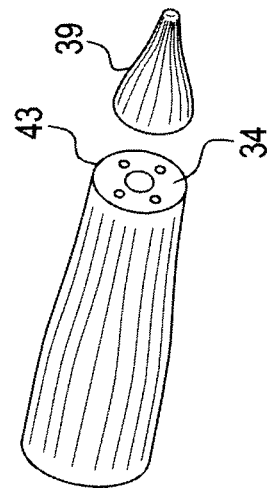
FIG. 13 is a perspective of the finished part with the nosecone being removed along the interface between the nosecone and attachment plate.

In FIG. 13, the sacrificial nosecone 39 is then removed by cutting along the seam 43 between the edge of the attachment plat and the nosecone.

Figure 14:
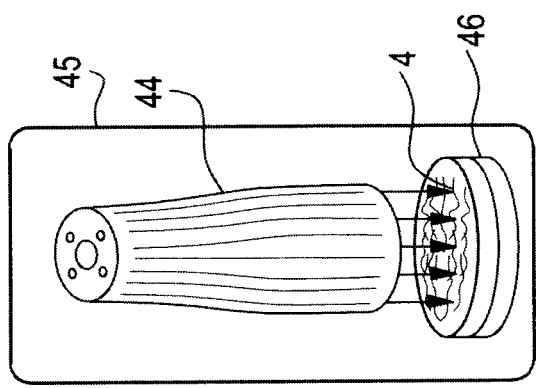
FIG. 14 is a schematic side view of the assembled part in an oven, with wax being removed from the interior.

In FIG. 14, the socket assembly 44 is placed, proximal end down, in oven 45, and heated to remove the wax 4, which drains into recovery tray 46 where it can be recycle for used for production of additional blank molds 8. Alternatively, if the mold was developed using water soluble mold material, the interior of the mold can be flushed out with water. The finished product is then cleaned.

Figure 15:
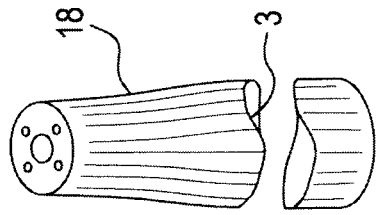
FIG. 15 illustrates the last step in the process where the part is trimmed to remove excess braided material from the finished socket.

FIG. 15 illustrates the final step, where the socket is trimmed at the proximal end along trim line 3 established in the original 3-D model 1.

Figure 16:
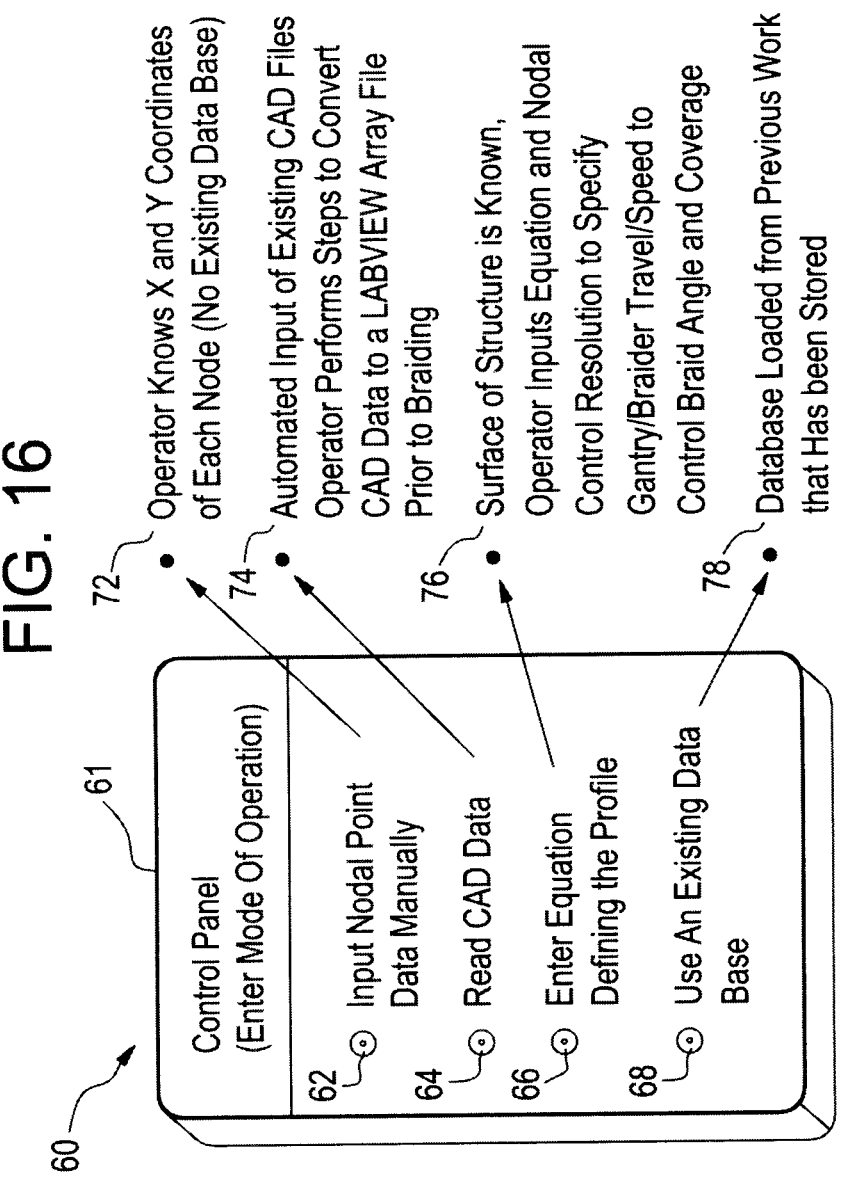
FIG. 16 illustrates four modes of control in the Mentis Sciences Computer Automated Braiding System (MSCABS) system.

FIG. 16 illustrates four modes 60 of control selected in a control panel 61. A user inputs desired net shapes of a structure either manually 62, from a CAD data transfer 64, or from an equation defining the profile 66, or from an existing tool data base 68. Once started the computer would then control the process of laying fiber onto a mandrel at correct orientations to the mandrel for the total number of layers required. During this process the braiding system would automatically control speed, direction of travel, and other parameters associated with braiding.

Four modes of operation have been defined and programmed to allow the operator of the braiding system to run in a mode which best fits desired net shape product requirements and available resources (i.e., existing CAD files). The four modes the operator can choose from are 1) Manual Nodal Input 62; 2) Automated Nodal Input (CAD to Braid) 64; 3) Surface Equation Input 66; or 4) Use of an Existing Data Base 68.

The manual mode 62 is used when the operator knows and enters the X and Y coordinates of each node 72. The CAD data transfer mode 64 is used after automated input of existing CAD files with the operator performing steps to convert the CAD data to a LABVIEW array file prior to braiding 74. The equation mode 66 is used when the operator inputs a known equation and nodal control resolution to specify the speeds at which the gantry and the braider operate to control braid angle and coverage 76. The data base mode 68 is used when data from previous work has been stored and can be loaded by the operator 78.

The selection of any one of the four modes automatically launches program code that prompts the operator to enter required information for fully automated braiding to take place. FIG. 16 shows the control panel used by the operator to select the desired braid control method. The manual nodal input mode 62 is used when the operator knows the X and Y coordinates of each node along the profile of a structure, but does not have an existing data base. This mode of operation will aid the operator by allowing them to input all nodal information, verify that each point was correctly entered via graphics and digital indicators, and to modify the data base if errors are made during data entry. Once the data base has been entered and verified, the data base can be saved for future use as is, or modified if necessary.

The second mode of operation is an automated nodal input (CAD to Braid) mode 66. This process has been defined to assist the operator in fabricating a structure with a given CAD file. The process requires the operator to perform a few basic steps to convert CAD data to a LABVIEW array file prior to braiding. The procedure was developed to read the profile from CADKEY into LABVIEW. The profile of a simple cone, for example, can be loaded into the braiding control system from a CAD file that was generated using CADKEY drafting software. Although this geometry could have easily been loaded using the manual input mode 62, it shows that any geometry with a large number of data points can be loaded successfully. As with the manual input mode 62, data loaded using this format can be stored for future applications if desired.

The third mode of operation called the equation input mode 64 is used when the surface of the structure to be braided is known. An example of this application would be the fabrication of a bullet shaped structure where the operator simply inputs the equation that defines the profile (i.e., $Y=Ax^4+Bx^3+Cx^2+Dx+E$). Where "Y" is the radius of the braided structure as a function of the "X", the distance along the structure's braiding axis. Once entered, the system then graphically displays the shape to be manufactured, and prompts the operator to input the nodal control resolution required. The nodal resolution is required so that the braiding control system initiates control signals to the Braider at the desired Gantry travel distance. This will allow either the braid angle or coverage factor to be precisely controlled along the length of the structure. The last mode of operation 68 allows the operator to use an existing database. The database can be loaded from previous work that has been stored. The data after being loaded can be viewed and confirmed using graphs and digital displays prior to starting the braider.

FIGS. 17a, 17b, and 17c illustrate a method of applying resin is according to the conventional VARTM method wherein a cone-shaped, flexible PVA bag 79 (FIG. 17a) is secured around the exterior of mold 13 containing the layers of braided fiber, mounted vertically on mounting fixture 80 with the bottom of the bag secured to a ring 81 such that a vacuum can be pull on the bag via tube 82 attached to vacuum pump 33. In FIG. 17b, by cutting open the PVA bag at the top and forming a small reservoir 83, resin 84 can then be poured into the reservoir at the top, which, when assisted with vacuum applied at the bottom promotes a flow of resin 84 thought the braided fiber material from top to bottom. This process can be assisted manually by the technician "massaging" the resin manually down the socket assembly to assure the fiber laminate is fully wetted. FIG. 17c shows the removal of the PVA bag. From this point on, the process continues as shown in FIGS. 11-15.

Forces generated by body weight while standing, walking or running have to be carried by the soft tissue of the residual limb, which when unevenly distributed can lead to discomfort and ultimately the breakdown of skin tissue. In order to forestall this, loads must be distributed over pressure tolerant areas such as the patella tendon, and with pressure relief provided over sensitive areas such as the fibula head. This can be accomplished in a number of ways, including, for example, use of a gel-type liner where pressure is applied to the entire surface of the limb with liner material redistributing weight by flow of gel of material.

Alternative methods however can be used with the braiding process to locally modify and strengthen the rigid socket wall to provide pressure relief through cut outs in the wall or utilizing other means to reduce contact pressure in sensitive regions such as bony prominences. This allows the load bearing areas to support the limb but cut outs or other means allowing a compliant surface to flex under the stresses of walking or running.

FIGS. 18a, 18b, and 18c illustrated how the braiding technology described in this invention facilitates the integration of compliant features into the socket wall to relieve in-socket pressure during walking and running, incorporating, for example, cut-outs or expandable features that can be added during the braiding process. FIG. 18a shows a variety of reinforcements shaped piece of graphite or fiberglass weave 85 can be added to reinforce the wall of the socket around a cut-out area 86. Several smaller disks 87 can be added around locations 88 where valves may be mounted to increase wall thickness to accommodate threaded fixtures. Ribbons of weave 89 can be added axially to support the overall structure in the axial direction 90 when multiple cut-outs are required. Tailored weaves 91 can be added to the proximal end of the socket 92, prior to trimming (FIG. 15) to thicken up that section so that there is not a sharp edge. When braiding a socket, most the structural and stiffness requirements may be met with only two graphite fiber braided layers, significantly lowering the weight and cost of the socket. But the thinness of this ply, adequate for the mid-section may be too sharp at the proximal end, requiring more plies to support a more rounded surface. In like manner, tailored weaves or tapes 91a can be added to the distal end of the socket 92a prior to the final layer of braided material to provide added strength to the junction of the attachment plate to the socket.

FIG. 18b, a side view of a cut-out (85 or 88), shows how multiple layers can be "feathered" to enhance smoothness of the transition, for example, from two layers to four layers in the case of the cut-outs. FIG. 18b shows the outer braided layer 93 with two patches (94 and 95) with decreasing diameters, sandwiched between the outer and inner layer 96. Voids are shown filled in with resin 97. This allows for a smooth transition.

FIG. 18c shows compliance features could be added to the wall of the socket to allow for expansion through cut-outs described previously. An appliance housing 98a is attached via screws or rivets to the reinforced wall of the socket 98b. The housing can contain foams or gels, or has been suggested in the literature a spring loaded flexible diaphragm 98d. The appliance can then be braided over with another layer of braided fiber 98e to enhance strength and appearance. Voids 98f can be filled in with resin during the VARTM process described above.

FIG. 19a shows a removable appliance 99a added to the baseline socket via an open-ended "pouch" 99b that is braided onto the socket wall 99c. The appliance 99a could be a removable electronics package and/or battery pack to power microprocessor driven motorized ankle or knee joints. The package can be removed through an opening at the top of the pouch 99d.

FIG. 19b shows the process for incorporating appliance 99a into the socket. A dummy surrogate 99e, the approximate size of the appliance 99a, is wrapped with PVA bag material 99f, that does not adhered to the surrogate. At this point, sculpted foam transition inserts 99g are adhered to the PVA covered surrogate so when braiding takes place, the fibers transition smoothly over the pouch exterior. Alternately, the PVA covered surrogate can be adhered directly to the socket with a foaming agent applied to the transition area and sculpted into shape before hardening.

After another layer or layers of braided fiber is applied, and resin is applied with the vacuum assisted transfer process shown in the FIG. 17, the product is cured and the surrogate electronics package along with its PVA wrapping material is remove 99h. This leaves the pouch open at the top for insertion of the real electronics package 99a.

A prosthetic truncated limb socket is produced using textile braiding techniques. first, producing truncated limb measurements are taken. A truncated limb-shaped mold or mandrel is machined from the measurements. A plastic film or thermoset layer is formed over the truncated limb-shaped mold or mandrel. A prosthetic limb attachment plate is secured to the limb-shaped mandrel. Fibrous tows are braided over at least part of the attachment plate and over the limb-shaped mandrel. A braided prosthetic truncated limb socket results after removing the limb-shaped mandrel from an interior of the braided socket. The tows are formed of fibers. Each tow may have about 3,000, 6,000 or 12,000 fibers. Carbon fibers are surface treated and sized.

The new method includes impregnating the braided socket with resin and curing and hardening the resin.

A sleeve is placed around the braided socket. Pressure is reduced within the sleeve. Resin is introduced at one end of the sleeve around the braided socket. The resin is forced along the braided socket within the sleeve. The sleeve is removed and the resin is cured.

One form of the impregnating uses brushing, spraying, or manually laying resin on braided layers and placing a sleeve around the braided socket. Reducing pressure within the sleeve compact the socket until the resin is cured.

Braiding the fibrous tows back and forth over the limb-shaped mandrel forms plural braided layers of fibrous material. Woven cloth strips or cutouts are placed on previously braided layers of woven material, and the cloth strips are secured in place with additional layers of braided material.

Some attachment plates have wings, and the braiding includes braiding around part of the attachment plate and over the wings of the attachment plate.

Beginning braiding at a large open end of the socket, braiding over a side of the attachment plate and back and forth over the side of the attachment plate and over the socket strengthens the important connection.

Braiding proceeds over a side of the attachment plate and back and forth over the side of the attachment plate and over the socket over the mold or mandrel made of an easily removable and reusable wax or an easily removable soluble casting material created by a computer aided design file on a numerically controlled machine tool.

One embodiment provides a cone in axial extension of the limb shape and attachment plate. The cone has an end adjacent the attachment plate. The braiding continues over the cone, the attachment plate and the limb-shaped mandrel. Finally the cone and the braiding over the cone are removed from the attachment plate.

A thermoset layer covers the truncated limb-shaped mandrel.

The truncated limb-shaped mandrel and the thermoset layer are mounted on a gantry braider. The braiding includes braiding a first biaxial or triaxial layer on the thermoset layer, and braiding a second biaxial or triaxial layer on the first biaxial or triaxial layer. The strength and stiffness of the prosthetic socket are controlled by controlling gantry and braider speeds and tension on the tow.

A prosthetic truncated limb socket is made by the methods described above.

A truncated limb braided socket has a hollow shape with an open end and a closed end. An attachment plate connected to the closed end for attaching a prosthetic limb part. The braided socket having braided fibrous tows and resin in the braided fibrous tows.

The braided fibrous tows are biaxially braided fibrous tows.

In another form, the braided fibrous tows are triaxially braided fibrous tows.

The new socket has multiple braided layers of the braided fibrous tows. Cloth strips extending along the socket between braided layers from the closed end toward the open end, and circular or other shaped cutouts are placed along the braided socket to reinforce areas in the socket.

The cloth strips or shaped cutouts are positioned between layers of the multiple braided layers.

Wings of the attachment plate extend along the socket from the closed end toward the open end. The wings of the attachment plate are positioned between layers of the multiple braided layers.

Foams, diaphragms, or appliances are added to the socket and braided over to secure the foams, diaphragms, or appliances in place with additional layers of braiding.

A dummy insert is covered with impervious layers of plastic wrap that are braided over and then removed after the resin has cured, thereby forming a pocket for insertion of electronic circuit boards, power supplies and batteries.

While the invention has been described with reference to specific embodiments, modifications and variations of the invention may be constructed without departing from the scope of the invention, which is defined in the following claims.

We claim:

1. Apparatus comprising:
 a truncated limb braided socket having:
 a hollow shape with an open end and a closed end, and
 an attachment plate connected to the closed end for attaching a prosthetic limb part,
 the braided socket having multiple braided layers of braided fibrous tows and resin in the braided fibrous tows, and having cloth strips extending along the socket from the closed end toward the open end and circular or other shaped cutouts placed along the braided socket to reinforce areas in the socket, wherein the cloth strips or shaped cutouts are positioned between layers of the multiple braided layers.

2. The apparatus of claim 1, further comprising wings of the attachment plate extending along the socket from the closed end toward the open end.

3. The apparatus of claim 2, wherein the wings of the attachment plate are positioned between layers of the multiple braided layers.

4. The apparatus of claim 1, wherein foams, diaphragms, or appliances are added to the socket and braided over to secure the foams, diaphragms, or appliances in place with additional layers of braiding.

5. The apparatus of claim 1, wherein the braided socket is braided over a truncated limb shape.

6. The apparatus of claim 5, wherein the truncated limb shape is mounted on a gantry, wherein a braider braids the fibrous tows on the truncated limb shape.

7. The apparatus of claim 6, wherein the truncated limb shape mounted on the gantry is a replica of an individual's truncated limb.

8. Apparatus comprising:
 a truncated limb braided socket having:
 a hollow shape with an open end and a closed end, and
 an attachment plate connected to the closed end for attaching a prosthetic limb part,
 the braided socket having braided fibrous tows and resin in the braided fibrous tows, wherein at least one dummy insert is covered with impervious layers of plastic wrap that have been braided over and removed after the resin has cured, thereby forming a pocket for insertion of electronic circuit boards, power supplies and batteries.

9. The apparatus of claim 8, wherein the braided socket is braided over a truncated limb shape.

10. Apparatus comprising:
 a prosthetic truncated limb socket made by:
 providing truncated limb measurements,
 forming a truncated limb shape from the measurements,
 providing a thermoset layer over the truncated limb shape,
 mounting the truncated limb shape with thermoset layer on a gantry,
 securing a prosthetic limb attachment plate to the truncated limb shape,
 inserting the gantry with the truncated limb shape and the attachment plate into a braider,
 attaching fiber tows from the braider to the truncated limb shape,
 rotating the braider,
 repeatedly translating the gantry and the limb shape and attachment through the braider,
 translating the gantry back and forth through the braider where the attachment plate is secured to the limb shape adding cloth strips over the braid where the attachment plate is secured to the limb shape translating the gantry back and forth through the braider over the cloth strips,
 braiding fibrous tows over at least part of the attachment plate and over the limb shape, and wherein the braiding comprises braiding a first biaxial or triaxial layer on the thermoset layer, and braiding a second biaxial or triaxial layer on the first biaxial or triaxial layer, and forming a braided prosthetic truncated limb socket, and removing the limb shape from an interior of the braided socket.

11. A method comprising producing a prosthetic truncated limb socket utilizing textile braiding techniques including:

producing truncated limb measurements, forming a truncated limb shape from the measurements, forming a plastic film or thermoset layer over the truncated limb shape, providing a prosthetic limb attachment plate secured to the limb shape, braiding fibrous tows over at least part of the attachment plate and over the limb shape, braiding the fibrous tows back and forth over the limb shape to form braided layers of fibrous material, placing woven cloth strips or cutouts on previously braided layers of woven material, securing the cloth strips in place with additional layers of braided material, and forming a braided prosthetic truncated limb socket, and removing the limb shape from an interior of the braided socket.

12. The method of claim 11, further comprising impregnating the braided socket with resin and curing and hardening the resin.

13. The method of claim 12, wherein the impregnating comprises:

placing a sleeve around the braided socket, reducing pressure within the sleeve introducing the resin at one end of the sleeve around the braided socket, forcing the resin along the braided socket in the sleeve, curing the resin, and removing the sleeve.

14. The method of claim 12, wherein the impregnating comprises:

brushing, spraying, or manually laying resin on the braided layers, placing a sleeve around the braided socket, and reducing pressure within the sleeve until the resin is cured.

15. The method of claim 1, wherein the providing the attachment plate comprises providing an attachment plate with wings and wherein the braiding comprises braiding around the attachment plate and over the wings of the attachment plate.

16. The method of claim 1 further comprising beginning braiding at a large open end of the socket, braiding over a side of the attachment plate and back and forth over the side of the attachment plate and over the socket.

17. The method of claim 1, further comprising braiding over a side of the attachment plate and back and forth over the side of the attachment plate and over the socket over the truncated limb shape that includes a mold or mandrel made of an easily removable and reusable wax or an easily removable soluble casting material created by a computer aided design file on a numerically controlled machine tool.

18. The method of claim 1 further comprising providing a cone in axial extension of the limb shape and attachment plate, the cone having an end adjacent the attachment plate and wherein the braiding comprises braiding over the cone, the attachment plate and the limb shape, and removing the cone and the braiding over the cone from the attachment plate.

19. The method of claim 1, comprising providing the thermoset layer on the truncated limb shape.

20. The method of claim 1 further comprising mounting the truncated limb shape and thermoset layer on a gantry braider and wherein the braiding comprises braiding a first biaxial or triaxial layer on the thermoset layer, and braiding a second biaxial or triaxial layer on the first biaxial or triaxial layer.

21. A prosthetic truncated limb socket made by the method of claim 20.

* * * * *